United States Patent
Jacobs et al.

(10) Patent No.: US 11,141,502 B1
(45) Date of Patent: *Oct. 12, 2021

(54) SYSTEMS AND METHODS FOR ATOMIZING LIQUIDS

(71) Applicants: IDEAL JACOBS CORP., Maplewood, NJ (US); WISTWELL, INC., Maplewood, NJ (US)

(72) Inventors: Andrew C. Jacobs, Short Hills, NJ (US); Todd Sherman, South Orange, NJ (US); Nicholas John Rafanello, Morris Plains, NJ (US)

(73) Assignees: Ideal Jacobs Corp., Maplewood, NJ (US); Wistwell, Inc., Maplewood, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 17/146,611

(22) Filed: Jan. 12, 2021

Related U.S. Application Data

(63) Continuation of application No. 17/034,039, filed on Sep. 28, 2020, now Pat. No. 10,888,634.

(51) Int. Cl.
*A61L 9/12* (2006.01)
*A61L 9/14* (2006.01)
*B01F 3/04* (2006.01)

(52) U.S. Cl.
CPC ............... *A61L 9/122* (2013.01); *A61L 9/14* (2013.01); *B01F 3/0407* (2013.01); *A61L 2209/111* (2013.01); *A61L 2209/134* (2013.01)

(58) Field of Classification Search
CPC ........... A61L 9/122; A61L 9/14; B01F 3/0407
See application file for complete search history.

(56) References Cited

U.S. PATENT DOCUMENTS

2019/0192717 A1   6/2019   Harwig

FOREIGN PATENT DOCUMENTS

JP   2018183468 A   11/2018

*Primary Examiner* — Robert A Hopkins
(74) *Attorney, Agent, or Firm* — Kelley Drye & Warren LLP

(57) ABSTRACT

Atomizers and methods for operating atomizers for dispersing vapor into the ambient air are disclosed. Liquid from a vessel connected to the atomizer may be pumped to a first chamber having an atomizing element at or near the bottom of the first chamber. The atomizing element may convert the liquid to a vapor, and a fan may push air into the first chamber, causing the vapor to be dispersed into the ambient air through apertures at or near the top of the first chamber. Liquid remaining in the first chamber may be pumped back to the vessel, while the fan continues to run to dry the components in the first chamber.

20 Claims, 3 Drawing Sheets

SYSTEMS AND METHODS FOR ATOMIZING LIQUIDS

CROSS-REFERENCE TO RELATED APPLICATIONS

This application is a continuation of U.S. patent application Ser. No. 17/034,039, filed on Sep. 28, 2020. The entire contents of that application are incorporated herein by reference.

BACKGROUND OF THE INVENTION

Liquids may be dispensed by atomization, vaporization or aerosol generation for many purposes. Fluid dispensing devices have been used, for example, in the administration of medicines, the diffusion of cosmetic products (e.g., perfumes) and for disinfection, odor generation, or humidification.

Regarding disinfection, easily communicable diseases, viruses, or bacteria may spread from one person to another through a variety of ways, including by touch; by contact with blood and other bodily fluids; by breathing in an airborne virus; or by being bitten by an insect. It is well-known that liquid disinfectant vaporized and dispersed into the air in droplets of sufficient size may help prevent transmission by several of these means. For example, U.S. Patent Publication No. 2003/0143110 discloses a device that uses high frequency ultrasonic energy for the atomization of disinfectant solutions.

However, the need exists for an atomizing system that is able to check whether the solution to be atomized is provided in an approved vessel, is approved for the application for which it is intended, and/or has an acceptable pH before the atomizer converts the solution to vapor. The need also exists for an atomizer that can perform self-maintenance operations by transferring unused solution back to a source vessel, and by drying the atomizing element when the atomization process is complete.

SUMMARY OF THE INVENTION

The present invention is directed to an atomizer for dispersing vapor into the ambient air surrounding the atomizer. The vapor may be, for example, a disinfecting solution capable of inhibiting the spread of communicable diseases.

One objective of the present invention is to provide an atomizer that includes a pump capable of drawing liquid from a vessel, delivering the liquid to a first chamber having an atomizing element, and returning unused liquid from the chamber to the vessel when the atomization process is complete.

Another objective of the present invention is to provide an atomizer having a fan capable of delivering air to the first chamber, and which continues to run while the pump returns unused liquid from the first chamber to the vessel. Continuing to run the fan while the pump returns unused liquid to the vessel helps ensure the unused liquid can be drawn by the pump. It also helps dry the first chamber and the components therein.

A vessel containing a liquid to be atomized may be connected to the atomizer. The vessel may have an identifier on, or embedded in, an outer wall of the vessel. It is another object of the present invention to provide an atomizer having a scanner capable of scanning the vessel identifier. The scanner may read data from the identifier, and one or more processors within the atomizer may determine, based on that data, whether to pump liquid from the vessel to the chamber to atomize the liquid.

The atomizer may include a pH sensor to determine the pH of liquid in the vessel. The atomizer may use pH information provided by the sensor to determine whether to pump liquid from the vessel to the chamber to atomize the liquid. The atomizer may further include a second chamber containing a liquid that may be delivered to the vessel to, for example, change the pH of the liquid in the vessel.

Numerous variations may be practiced in the preferred embodiment.

BRIEF DESCRIPTION OF THE DRAWINGS

A further understanding of the invention can be obtained by reference to exemplary embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

DETAILED DESCRIPTION OF THE INVENTION

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiments for purposes of disclosure and to provide a basis for the claims herein, which define the scope of the invention. It should also be noted that, as used in the specification and the appended claims, the singular forms "a", "an", and "the" include plural referents unless the context clearly indicates otherwise.

Use of the term "exemplary" means illustrative or by way of example, and any reference herein to "the invention" is not intended to restrict or limit the invention to the exact features or steps of any one or more of the exemplary embodiments disclosed in the present specification. Also, repeated use of the phrase "in one embodiment," "in an exemplary embodiment," or similar phrases do not necessarily refer to the same embodiment, although they may. Terms like "preferably," "commonly," and "typically," are not used herein to limit the scope of the claimed invention or to imply that certain features are critical, essential, or even important to the structure or function of the claimed invention. Rather, those terms are merely intended to highlight alternative or additional features that may or may not be used in a particular embodiment of the present invention.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Figure 1:
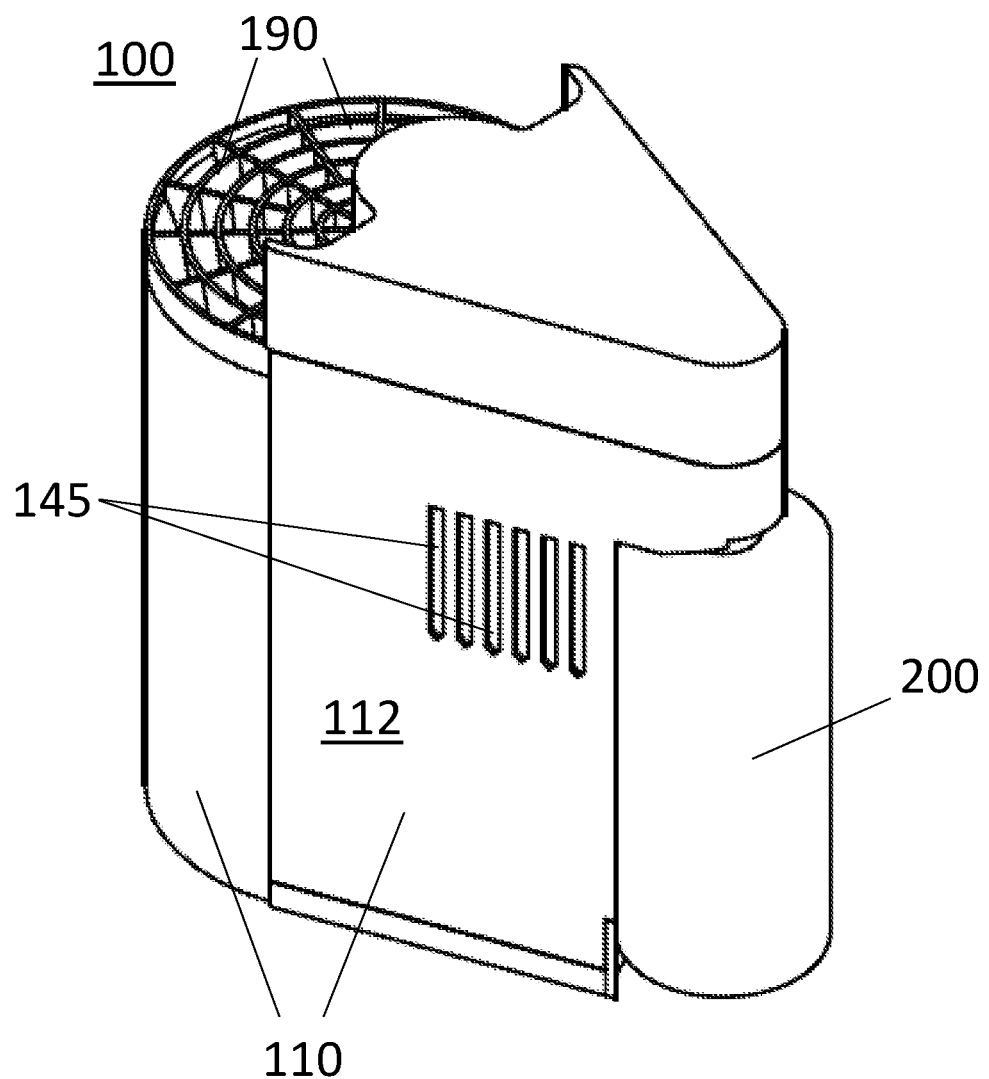
FIG. 1 depicts a perspective view of an embodiment of the invention.
Figure 2:
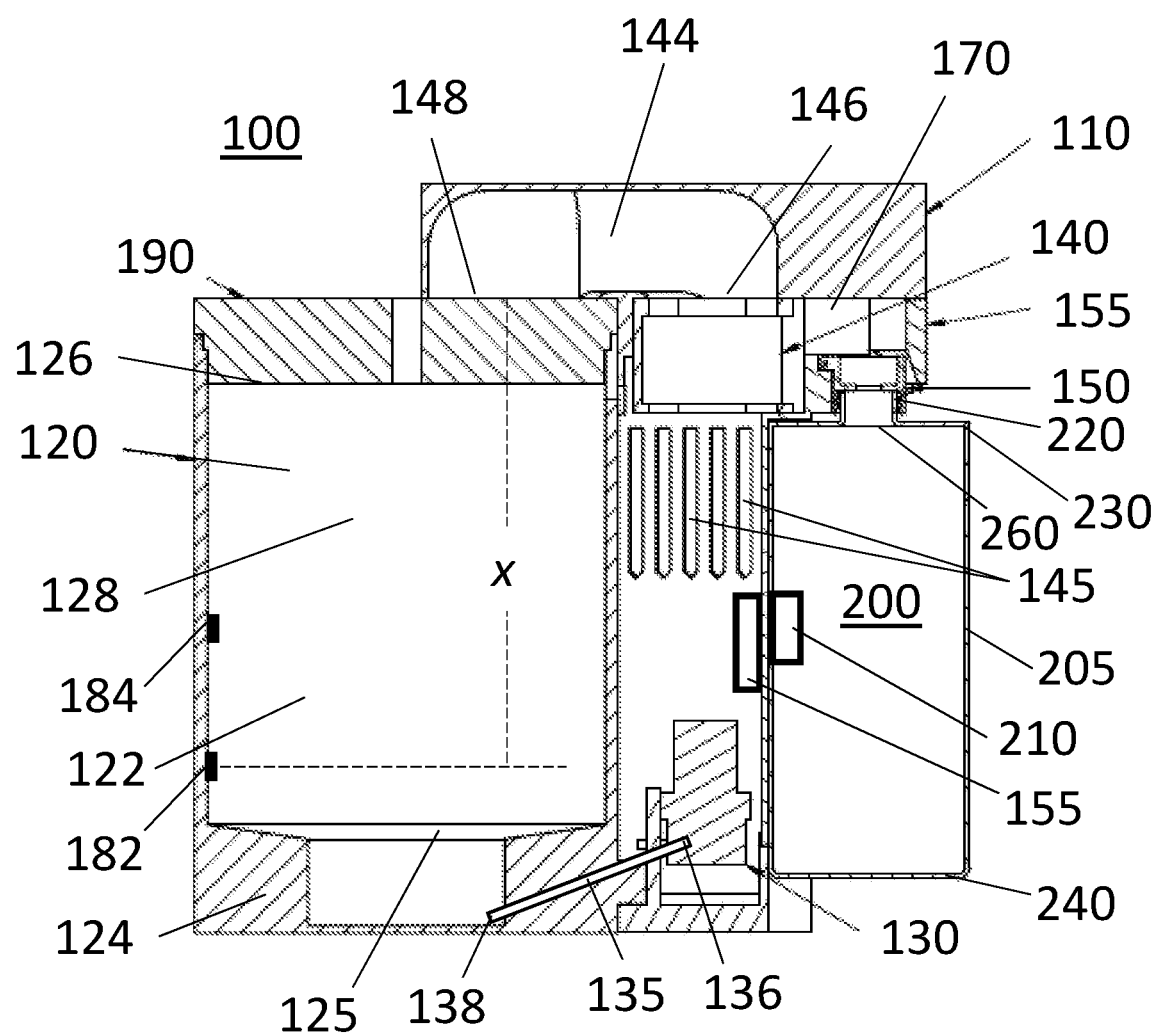
FIG. 2 depicts a cross-sectional view of the embodiment shown in FIG. 1.
Figure 3:
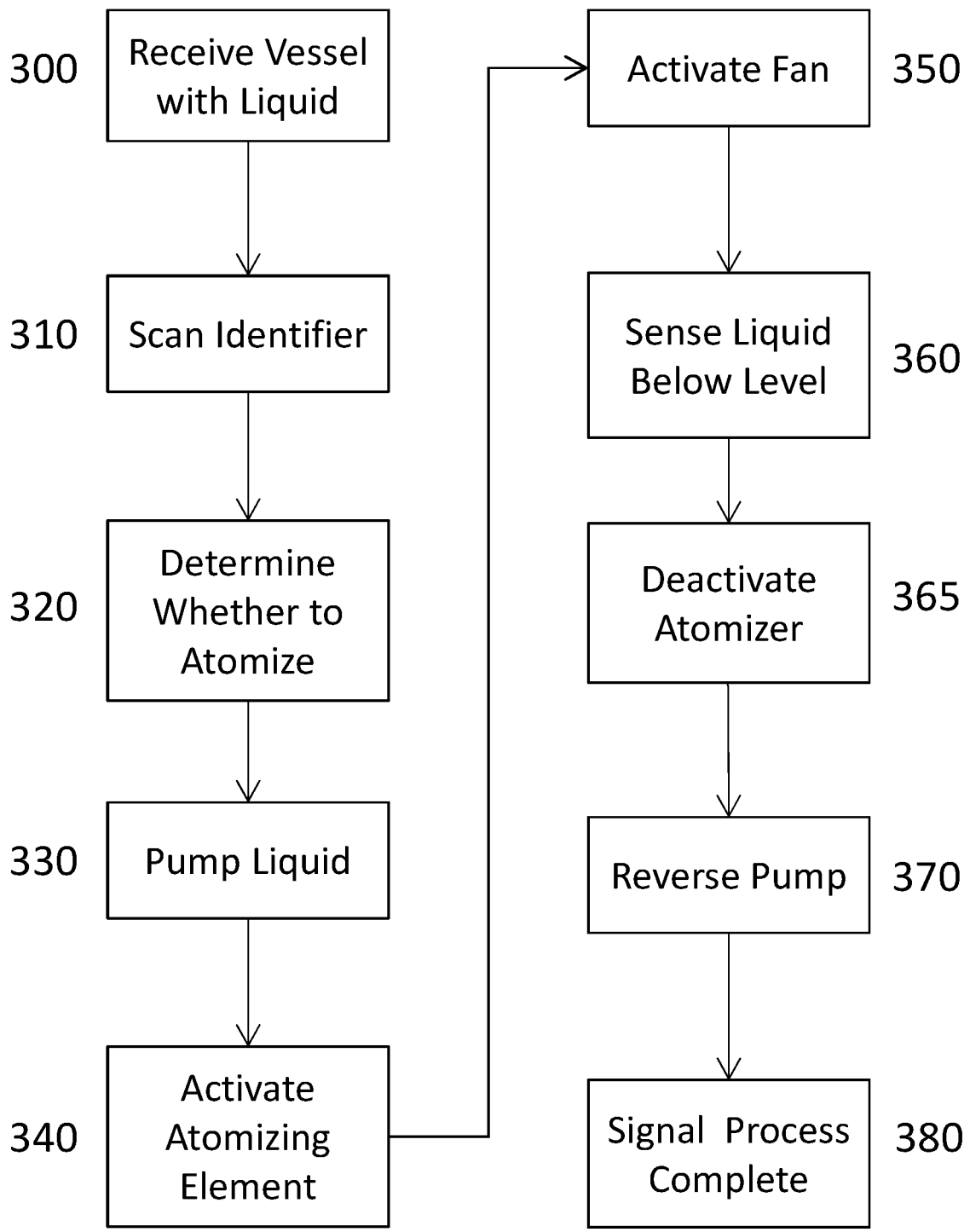
FIG. 3 is a flowchart of a method according to the present invention.

FIGS. 1 and 2 depict an atomizer (100) in accordance with the present invention. FIG. 2 is a cross-sectional view of atomizer (100) depicted in FIG. 2. Atomizer (100) includes a housing (110) having one or more outer walls (112). Within housing (110) may be a first chamber (120), an atomizing element (125), a pump (130), a fan (140), a scanner (155), a first liquid sensor (182), a second liquid sensor (184), a non-transitory memory (not shown), and/or one or more processors (not shown) coupled to the non-transitory memory. Pump (130), fan (140), atomizing element (125), scanner (155), first liquid sensor (182) and/or second liquid sensor (184) may be in electronic communication with the one or more processors and/or the non-transitory memory. Power may be supplied to one or more of the components of atomizer (100) identified herein from, for example, a battery located within or attached to housing (110) and/or from an electric outlet via a power cord attached to housing (110).

First chamber (120) may be formed from one or more chamber walls (122), that extend from bottom end (124) of first chamber (120) to top end (126) of first chamber (120), forming an inner space (128) therein. The one or more chamber walls (122) of first chamber (120) may be arranged in any suitable shape, for example, in a circle, an oval, a rectangle, a square, or an octagon.

At or near bottom end (124) of first chamber (120) may be an atomizing element (125). Atomizing element (125) may comprise, for example, a piezoelectric transducer that may be driven by, for example, an AC power supply.

In the top end (126) of first chamber (120) or in the one or more chamber walls (122) of first chamber (120) may be one or more apertures (190). Apertures (190) may allow the inner space (128) within first chamber (120) to be in fluid communication with the ambient air surrounding atomizer (100). One or more apertures (190) may be oriented so as to cause a gas passing through the one or more apertures (190) to be directed in a plurality of directions.

Atomizer (100) may further include a vessel port (150). Vessel port (150) may be capable of receiving the opening of a vessel (200), such as a bottle, canister, can, container, or capsule. Vessel (200) may contain a liquid. For example, vessel (200) may contain a liquid having disinfecting properties.

Vessel port (150) may be attached to atomizer (100) by a hinge (155). Hinge (155) may allow vessel port (150) to be angled away from atomizer (100) to allow easier access to vessel port (150) and facilitate attaching vessel (200) to vessel port (150).

Vessel (200) may have one or more outer walls (205) that extend from a top (230) to a bottom (240). Vessel (200) may have a generally cylindrical shape. Vessel (200) may have a constant or generally constant cross-section from top (230) to bottom (240). Alternatively, vessel (200) may have a shape that does not comprise a constant or generally constant cross-section from top (230) to bottom (240). Top (230) and/or bottom (240) may taper or curve toward the center axis of vessel (200).

Top (230) of vessel (220) may have an aperture (260). Aperture (260) may lead to a neck (220) that may have the form of a hollow cylinder with open ends. A cap (not shown) may enclose neck (220) when vessel (200) is not connected to atomizer (100), so as to prevent the liquid within vessel (200) from spilling out of vessel (200) and/or from becoming contaminated by the introduction of elements from outside vessel (220). Additionally or alternatively, the top of neck (220) may be sealed by a removable cover. The removable cover may be a plastic cover having, for example, the same structure as covers commonly used to seal milk cartons and other containers.

Vessel (200) and/or vessel port (150) may have one or more connection elements capable of releasably or permanently joining vessel (200) to vessel port (150). The vessel port may, for example, have one or more walls that form a cylinder having an outer surface and an inner surface. To the extent vessel (200) has a neck (220), a screw thread (not shown) may extend from the outer and/or inner surface of neck (220). To the extent that vessel (200) does not have a neck (220) a screw thread (not shown) may extend from the inner surface of aperture (260). The screw thread on neck (220) and/or the screw thread on the inner surface of aperture (260) may be capable of mating with a screw thread (not shown) on the outer or inner surface of vessel port (150). Additionally or alternatively, one or more protrusions (not shown) may extend from the inner or outer surface of neck (220) and/or the inner surface of aperture (260). The protrusions may be capable of mating with one or more complementary slots in one or more walls of vessel port (150), forming a bayonet connection. Additionally or alternatively, neck (220) and/or the inner surface of aperture (260) may have one or more slots that are capable of mating with one or more protrusions on the inner and/or outer walls of vessel port (150), forming a bayonet connection. Alternatively, vessel (200) or neck (220) of vessel (200) may connect to atomizer (100) by snapping to vessel port (150).

Vessel (200) may have one or more identifiers (210). The one or more identifiers (210) may be, for example, attached to, printed on, and/or embedded in one or more of the outer walls (205), top (230), and/or bottom (240) of vessel (200). Each of the one or more identifiers (210) may be, for example, a QR code, a bar code, an RFID tag, or an NFC chip. To the extent that vessel (200) has more than one identifier (210), each identifier may be of a different type and may be attached to vessel (200) in a different way. For example, vessel (200) may have a bar code printed on bottom (230) and an RFID tag embedded in an outer wall (205).

Atomizer (100) may further include a scanner (155). Scanner (155) may be, for example, located in or attached to an outer wall (112) of atomizer (100). Scanner (155) may be positioned to allow it to read and/or transmit data to identifier (210) on vessel (200). Scanner (155) may be located above, below, or to the side of vessel (200) when vessel (200) is connected to vessel port (150). The connection elements discussed above for vessel (200) and vessel port (150) (e.g., screw threads, a bayonet connection, a snap connection) may cause vessel (200) to be oriented in a particular direction and/or oriented in a particular rotation so that, for example, when vessel (200) is connected to vessel port (150), identifier (210) is facing in a particular direction, such as toward scanner (155), and/or is located in proximity to scanner (155). A screw thread on neck (220) and/or a screw thread on vessel (200) and/or a bayonet connection formed between vessel port (150) and vessel (200) may cause vessel (200) to rotate to a particular orientation when vessel (200) is connected to vessel port (150). That orientation may cause identifier (210) to be adjacent to scanner (155) as shown in FIG. 2.

A first tube (not shown) may lead from pump (130) to vessel port (150). The first tube may extend from a first end connected to pump (130) to a second end that extends though vessel port (150). When a vessel (200) is connected to vessel port (150) the second end of the first tube may extend into vessel (200), and preferably to the bottom or near to the bottom of vessel (200).

A second tube (135) may lead from pump (130) to first chamber (120). The second tube may extend from a first end (136) connected to pump (130) to a second end (138). The second end (138) of the second tube may extend through a chamber wall (122) of first chamber (120), at or near bottom end (124) of first chamber (120).

When pump (130) is activated it may be capable of drawing liquid from vessel (200), through the first tube, and forcing the liquid through the second tube, into first chamber (120). Pump (130) may be further capable of pumping liquid in the reverse direction, i.e., from first chamber (120), through the second tube, through the first tube, and into vessel (200). Pump (130) may be a peristaltic pump, capable of pumping liquid in both directions described above.

Fan (140) may be an electric fan. An air passage (144) may extend from a first end (146) at or near fan (140) to a second end (148) at or near first chamber (120). Air passage (144) may be integrated as part of housing (110) as shown in FIG. 2, or may comprise a tube or other passage that extends outside of housing (110).

Preferably second end (148) of air passage (144) is located at or near top end (126) of first chamber (120). Second end (148) of air passage (144) may be oriented so as to direct air exiting air passage (144) through second end (148) in the direction of bottom end (124) of first chamber (120). Alternatively, second end (148) of air passage (144) may be oriented so as to direct air exiting air passage (144) through second end (148) in the direction of a chamber wall (122) of first chamber (120).

One or more apertures (145) may be located in one or more outer walls (112) of housing (110). The one or more apertures (145) may cause air outside atomizer (100) (ambient air) to be in fluid communication with fan (140). Fan (140) is capable of blowing air through air passage (144), from first end (146) to second end (148) and into first chamber (120). The air blown through air passage (144) may be ambient air drawn through one or more apertures (145), into housing (110), before being blown by fan (140) through air passage (144).

A first liquid sensor (182) may be located in and/or attached to a chamber wall (122) of first chamber (120). A second liquid sensor (184) may also be located in and/or attached to a chamber wall (122) of first chamber (120). Second liquid sensor (184) may be located above first liquid sensor (182). Additionally, or alternatively, a float may be included in first chamber (120) to measure the height of the liquid therein. First liquid sensor (182) and/or a float may provide an indication when the liquid pumped into first chamber (120) has reached as sufficient level to begin atomizing the liquid. Second liquid sensor (184) and/or a float may provide an indication when the liquid level in first chamber (120) has reached a level at which the pump should cease pumping liquid into first chamber (120).

Preferably, second end (148) of air passage (144) may be located between six inches and 24 inches above first liquid sensor (182). Specifically, second end (148) of air passage (144) may be located approximately eight inches to twelve inches (x) above liquid sensor (182). Introducing air from fan (140) into first chamber (120) from that height causes desirable dispersion of the atomized vapor from first chamber (120), through one or more apertures (190) without undue disruption of the vapor droplets.

Atomizer (100) may include a second chamber (170) and a pH sensor (not shown). A third tube may extend from second chamber (170), through vessel port (150). When vessel (200) is attached to vessel port (150), the pH sensor and/or the third tube may extend into vessel (200). A liquid having a predetermined pH may be included in second chamber (170).

An atomizer (100) in accordance with the present invention may further include one or more visual indicators, such as one or more displays and/or one or more lights, and/or may include one or more audible indicators, such as one or more speakers or bells. The one or more processors may send a signal to the one or more visual or audible indicators to indicate to a user that, for example, the liquid in vessel (200) has been atomized and/or that the atomizing element (125) has been deactivated. Additionally or alternatively, atomizer (100) may have a transmitter capable of transmitting a signal over a wired connection or wirelessly to another device or to a device on a network, such as the internet. Additionally or alternatively, a system in accordance with the present invention may include an electric sign or other display that may be installed separate and apart from atomizer (100), such as outside of a room in which atomizer (100) is located. A transmitter in atomizer (100) may be capable of transmitting a signal to the sign or display. The sign or other display may indicate that the atomization process is completed.

FIG. 3 depicts a flow chart showing a method of operating an atomizer (100) in accordance with the present invention. At Step 300, a vessel (200) may be received by atomizer (100). Vessel (200) may be attached to atomizer (100) at a vessel port (150). For example, vessel (200) may have an extended opening at the top with a screw thread on the outer surface and/or a screw thread on the inner surface. The screw thread may mate with a screw thread on vessel port (150). As another example, vessel (200) may have an extended opening at the top with one or more protrusions that mate with one or more complementary slots in vessel port (150), forming a bayonet connection. Alternatively, vessel (200) may have one or more slots that mate with one or more protrusions on vessel port (150), forming a bayonet connection. Alternatively, vessel (200) may connecting to atomizer (100) by snapping to vessel port (150). The connection formed between the vessel and the vessel port may orient the vessel in a particular direction and/or rotation.

To the extent that the vessel has an identifier (210), at Step 310, a scanner (155) on or in the atomizer may read identifier (210). As noted above, identifier (210) may be, for example, a QR code, a bar code, an RFID tag, or an NFC chip. Scanner (155) may be capable of reading identifier (210)

and/or transmitting data to identifier (210) if, for example, identifier (210) is capable of receiving and/or storing data.

At Step 320, atomizer (100) may determine whether to begin atomization of the liquid in vessel (200) based on scan of a vessel identifier (155) and/or based on the pH of the liquid in vessel (200). If an identifier (210) is scanned by scanner (155), one or more processors in atomizer (100) may determine whether to initiate atomization of liquid in vessel (200) by, for example, (1) comparing data transmitted from scanner (155) to data stored in non-transitory memory in atomizer (100); (2) processing data transmitted from scanner (155) by an algorithm or other software stored in non-transitory memory; and/or (3) comparing data transmitted from scanner (155) to data stored at a remote server, such as a server accessed by a wireless (e.g., a Wi-Fi, cellular) or wired connection between atomizer (100) and the internet. Based on one or more of those processes, the one or more processors may initiate atomization of the liquid in vessel (200).

Additionally or alternatively, Step 320 may include determining whether to initiate atomization of the liquid in vessel (200) based on the pH of the liquid in vessel (200). For example, when vessel (200) is attached to atomizer (100) in Step 120, a pH sensor may be inserted into vessel (200). The pH sensor may send to the one or more processors data indicating the pH of the liquid in the vessel. The one or more processors may determine whether the pH level received from the pH sensor is the same as a predetermined level, above a predetermine level, below a predetermined level, or within a predetermined range. Based on one or more of those comparisons, the one or more processors may initiate atomization of the liquid in vessel (200). Alternatively, the one or more processors may cause liquid from second chamber (170) to be delivered to vessel (200) before initiating atomization of the liquid in vessel (200).

Additionally or alternatively, once atomization is initiated, the one or more processors in atomizer (100) may delay proceeding with one or more of the following Steps by a predetermined time. For example, if a user of atomizer (100) would prefer to exit the space in which the atomizer will disperse vapor before the vapor is dispersed, the delay may allow the user time to exit that space. The delay time may be predetermined (e.g. 30 seconds), may be selected by the user from a set of predetermined times (e.g., 30 seconds, one minute, five minutes), or may be set by the user by, for example, transmitting a time to atomizer (100) from a mobile device.

At Step 330, liquid within vessel (200) may be pumped from vessel (200) to a first chamber (120) of atomizer (100). Specifically, one or more processors may send a signal to pump (130), causing pump (130) to begin pumping liquid from within vessel (200) to first chamber (120). Preferably, the liquid would be introduced into first chamber (120) at or near the bottom of first chamber (120).

The liquid would be pumped into first chamber (120) until the level of fluid in first chamber (120) reaches a predetermined height within first chamber (120). For example, at Step 200, a first liquid sensor (182) within first chamber (120) may send a signal to the one or more processors indicating that the level of liquid within first chamber (120) has reached at least the height of the location of first liquid sensor (182) relative to the bottom of first chamber (120).

At Step 340, upon receiving a signal from first liquid sensor (182), the one or more processors may send a signal to atomizing element (125) or regulate a voltage sent to atomizing element (125), causing atomizing element (125) to begin atomization of the liquid. For example, atomizing element (125) may begin transmitting ultrasonic waves, which may be focused at the surface of the liquid, and may produce an ultrasonic "nozzle". This peak may discharge small droplets of the liquid.

At Step 350, fan (140) may be activated. Fan (140) may blow air through an air passage (144) to first chamber (120). Air may be drawn by the fan from one or more apertures (145) in one or more outer wall (112) of housing (110). Preferably, the air exiting air passage (144) enters first chamber (120) at or near the top end (126) of first chamber (120). Also, preferably, air exiting air passage (144) is directed downward, toward the bottom end (124) of first chamber (120).

While the atomizing element (125) and fan (130) are active, pump (140) may continue to pump liquid from vessel (200) to first chamber (120). At Step 360, a second signal may be received by the one or more processors from first liquid sensor (182), indicating that the liquid is no longer at the height of the first liquid sensor (182) in first chamber (120).

At Step 365, upon receiving the second signal from the first liquid sensor (182), the atomizing element may be deactivated.

At Step 370, pump (140) may be run in reverse. In other words, pump (140) may pump liquid from first chamber (120) to vessel (200). Preferably, fan (130) continues to operate while pump (140) is run in reverse to help force the liquid out of first chamber (120) and toward pump (140), and to help to dry the components in first chamber (120), including atomizing element (125).

At Step 380, a signal may be transmitted or displayed, indicating that the atomization process has completed. For example, a display or light on atomizer (200) may indicate that the atomizing element has been deactivated. Additionally or alternatively, and audible signal may be played. Additionally or alternatively, a signal may be transmitted over a wired connection or wirelessly to another device or to a device on a network, such as the internet. For example, an electric sign or other display may be installed on the outside of a room. When the atomization process is completed, atomizer (100) may transmit a signal to the sign or other display. The sign or other display may then indicate that the atomization process is completed.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system for dispersing vapor into ambient air, comprising:
an atomizer comprising:
a housing having a first chamber extending from a bottom end to a top end, said top end having one or more apertures in fluid communication with the ambient air, said bottom end having a atomizing element;

a fan;

an air passage capable of allowing air to travel from the fan to the first chamber;

a pump;

a vessel port;

a tube leading from the pump to the vessel port;

a non-transitory memory having a machine-readable medium comprising machine executable code;

one or more processors coupled to the memory; and a scanner in electronic communication with the one or more processors.

2. The system of claim 1 further comprising a vessel having an identifier capable of being scanned by the scanner.

3. The system of claim 2 wherein said one or more processors are configured to execute the machine executable code, wherein the machine executable code is capable of causing the one or more processors to receive from the scanner data read from the identifier.

4. The system of claim 3, wherein the machine executable code is capable of causing the pump to be activated.

5. The system of claim 1 wherein the scanner is a QR code reader.

6. The system of claim 1 wherein the scanner is an RFID reader.

7. The system of claim 1 wherein the scanner is an NFC chip.

8. The system of claim 1 wherein the scanner is a bar code reader.

9. The system of claim 1 wherein the atomizer further comprises a sensor capable of detecting the pH of the liquid in the bottle.

10. A system for dispersing vapor into ambient air, comprising:

an atomizer comprising:

a housing having a first chamber extending from a bottom end to a top end, said top end having one or more apertures in fluid communication with the ambient air, said bottom end having a atomizing element;

a fan;

an air passage extending from a first end near the fan to a second end at the first chamber;

a pump;

a vessel port;

a first tube leading from the pump to the vessel port;

a non-transitory memory having a machine-readable medium comprising machine executable code;

one or more processors coupled to the memory; and a telecommunications module in electronic communication with the one or more processors.

11. The system of claim 10 wherein the air passage is integrated as part of the housing.

12. The system of claim 10 wherein the air passage extends at last partly outside the housing.

13. The system of claim 10 wherein the second end of the air passage is located near the top end of the first chamber.

14. The system of claim 13 wherein the air passage is integrated as part of the housing.

15. The system of claim 13 wherein the air passage extends at last partly outside the housing.

16. The system of claim 13 wherein the second end of the air passage is oriented so as to direct air exiting the second end of said air passage in the direction of the bottom end of the first chamber.

17. The system of claim 16 wherein the air passage is integrated as part of the housing.

18. The system of claim 16 wherein the air passage extends at last partly outside the housing.

19. The system of claim 10 wherein the second end of the air passage is oriented so as to direct air exiting the second end of said air passage in the direction of the bottom end of the first chamber.

20. The system of claim 19 wherein the air passage extends at last partly outside the housing.

* * * * *